(12) United States Patent
Wu et al.

(10) Patent No.: US 10,687,826 B2
(45) Date of Patent: Jun. 23, 2020

(54) SURGICAL METHODS OF UNIVERSAL OSTEOTOMY DEVICE

(71) Applicant: A Plus Biotechnology Company Limited, New Taipei (TW)

(72) Inventors: Kai-Hsing Wu, Taipei (TW); Hsiang-Wei Lo, New Taipei (TW); Kun-Jhih Lin, Taichung (TW); Ping-Sheng Yu, Taipei (TW)

(73) Assignee: A PLUS BIOTECHNOLOGY COMPANY LIMITED, New Taipei (TW)

( * ) Notice: Subject to any disclaimer, the term of this patent is extended or adjusted under 35 U.S.C. 154(b) by 239 days.

(21) Appl. No.: 15/927,111

(22) Filed: Mar. 21, 2018

(65) Prior Publication Data
US 2019/0150950 A1 May 23, 2019

(30) Foreign Application Priority Data
Nov. 22, 2017 (TW) .............................. 106140620 A

(51) Int. Cl.
*A61B 17/15* (2006.01)
*A61B 17/17* (2006.01)
*A61B 17/80* (2006.01)
*A61B 90/50* (2016.01)

(52) U.S. Cl.
CPC .......... *A61B 17/157* (2013.01); *A61B 17/152* (2013.01); *A61B 17/1764* (2013.01); *A61B 17/155* (2013.01); *A61B 17/80* (2013.01); *A61B 90/50* (2016.02)

(58) Field of Classification Search
CPC .. A61B 17/157; A61B 17/152; A61B 17/1764
See application file for complete search history.

(56) References Cited

U.S. PATENT DOCUMENTS

| 4,502,474 A    | * | 3/1985 | Comparetto | ....... | A61B 17/1637 606/87 |
| 2006/0122617 A1 | * | 6/2006 | Lavallee   | ..............  | A61B 17/155 606/87  |
| 2011/0125157 A1 | * | 5/2011 | Sharkey    | ..............  | A61B 17/1764 606/92 |
| 2011/0213376 A1 | * | 9/2011 | Maxson     | ...............  | A61B 17/151 606/88  |
| 2012/0203233 A1 | * | 8/2012 | Yoshida    | ...............  | A61B 17/154 606/87  |

* cited by examiner

*Primary Examiner* — Christian A Sevilla
(74) *Attorney, Agent, or Firm* — Muncy, Geissler, Olds & Lowe, P.C.

(57) ABSTRACT

The present invention provides a surgical method of universal osteotomy device comprises the steps of: placing a first body component and a second body component on the surface of a bone; engaging an engaging member with a connecting member; inserting at least one aiming bone pin in at least one aiming hole to confirm the cutting direction; cutting along a guide slot to produce an osteotomy; spreading said osteotomy; placing a bone plate to maintain the osteotomy; wherein the surface of the first body component and the surface of the second body component have an average curvature of bone surface or a uniform curvature.

20 Claims, 17 Drawing Sheets

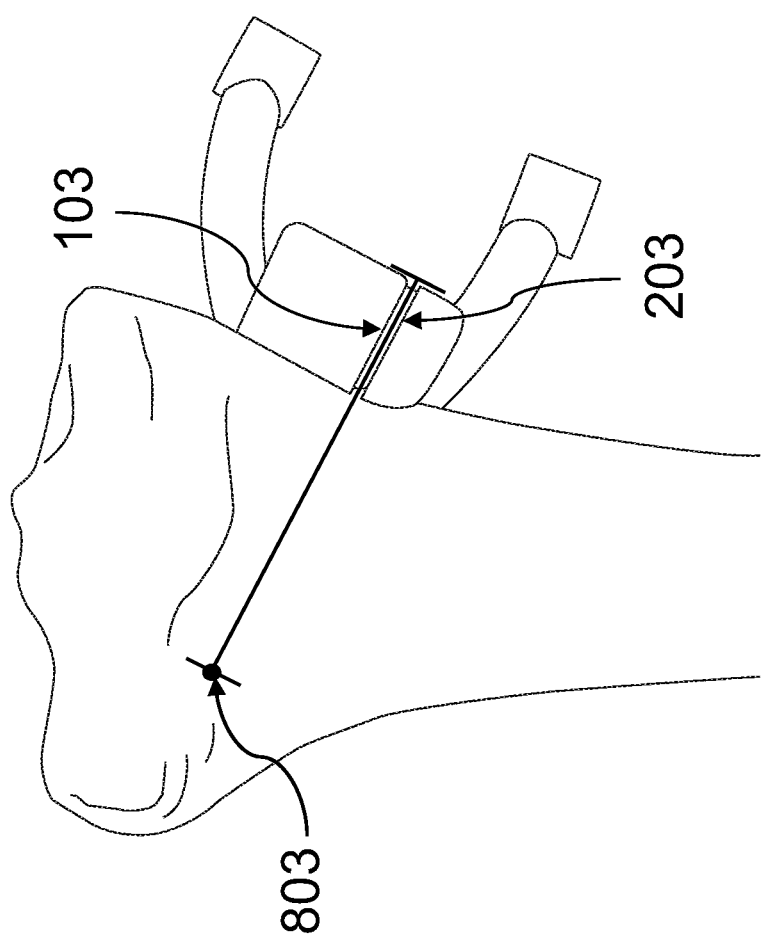

SURGICAL METHODS OF UNIVERSAL OSTEOTOMY DEVICE

BACKGROUND OF THE INVENTION

Technical Field

The present invention generally relates to a surgical method, and more particularly, to a surgical method of universal osteotomy device.

Description of Related Art

Under the continuous development of science and technology, human average life-span continues to be extended. But the articular cartilage is gradually worn with the aging of body. It causes the occurrence of degenerative joint disease called osteoarthritis. For patients with knee osteoarthritis in the observation of the X-ray, surgeons can find the uneven of joint surface, narrowed joint space and bone spurs. These pathological phenomena will cause the patients to produce pain, swelling, joint deformation, stiffness and other symptoms. This is the inevitable trend of physiological aging, it seems that the older the more likely to encounter the disease.

Taking knee for example, most common treatment of osteoarthritis is to implant the artificial joint to replace the knee joint surface, but large amount of soft tissue and hard tissue should be removed from the femur, the tibia and the patella to provide the fixation of metal and polyethelene implants. Due to the wear of the polyethylene component, the longevity of the artificial joint replacement is up to twenty years, but often complicated by postoperative infection, osteolysis and bone resorption. Resulting in the possibility of a revision surgery. Furthermore, in early-stage knee osteoarthritis, only the medial articular surface is affected. It is not necessary to replace all articular surface by artificial knee component. High tibial osteotomy is an alternative option for patients with medial knee osteoarthritis.

High tibial osteotomy is performed by a bone cutting plane in the proximal tibia of the knee on the medial side and making a wedge space by spreading the osteotomy. Finally, the construct is supported by bone plate fixation. Thus the biomechanical axis of the low limb can be corrected. In this procedure, the cartilage and bone stock around the knee joint are preserved. For the patients with medial knee osteoarthritis, it is a good option for surgical treatment.

The success for high tibial osteotomy relies on an appropriate bone cut including the cutting position, direction, depth, and the spreading height which are related to the correction angle. This surgery is highly technical demanded. At present, the surgeons perform the procedure based upon preoperative roentgenology images and their experience without any reference or guiding device. The above-mentioned parameters are also different for each patient. A personalized osteotomy device may be needed for a better control of the deformity correction.

However, if the overall osteotomy device was designed in accordance with the needs of patients, even though it has a customized geometry and design parameters and fully meet the needs of patients and other advantages, but it will take a long time for design estimation, a long time for manufacturing before surgery and other shortcomings. It may not be possible to provide immediate treatment in some emergency situations that are time-limited. Therefore, it may miss the critical period. So, how to allow surgeons can perform an accurate, rapid and convenient operation for joint osteotomy, it is an important issue, too.

The prior art of the present invention is TWM536526U. But, there is still room for improvement. For examples, it cannot take a non-invasive assessment of the correction angle when the surgery is performed, it cannot predict whether the angle of the osteotomy device placement is correct, it cannot directly maintain the angle of the osteotomy device placement, it may produce over-cutting, it may require preoperative evaluation for the geometry of the bone surface, it cannot be applied to the need for urgent surgery and the manufacturing process is complicated. The inventor of the present invention has further expanded its function and improved many of the techniques present in the prior art. Therefore, the inventor developed the surgical method of universal osteotomy device, the expansion of the function and improvement of the technology will be described in detail in the specification.

SUMMARY OF THE INVENTION

In view of the foregoing problems, the present invention provides a surgical method of universal osteotomy device. It is used to guide a saw blade to perform high tibial osteotomy, but not limited to, the surgical method of universal osteotomy device can be used for other bones, such as: femur, fibula, humerus, ulna, radius, clavicle, scapula and so on. The tibia is described in the preferred embodiment of the present invention. The device design features to assist the surgeon to determine the cutting position, direction, depth and the spreading height of the osteotomy precisely, rapidly and conveniently. Moreover, it can take a non-invasive assessment of the correction angle when the surgery is performed, it can predict whether the angle of the osteotomy device placement is correct, it can directly maintain the angle of the osteotomy device placement, and it can avoid over-cutting, it does not require preoperative evaluation for the geometry of the bone surface, it can be applied to the need for urgent surgery and the manufacturing process is simple. The osteotomy of the tibia after the operation of the present invention will have the precise cutting angle, the accuracy and the efficiency of the implementation. It can also be used for emergencies that are time-limited.

The present invention provides a surgical method of universal osteotomy device. The surgical method of universal osteotomy device is used to guide a saw blade to perform high tibial osteotomy, but not limited to, it can also be applied to other bones. According to the embodiment of the present invention, the surgical method of universal osteotomy device comprises the steps of: placing a first body component and a second body component on the surface of a bone; engaging an engaging member with a connecting member; inserting at least one aiming bone pin in at least one aiming hole to confirm the cutting direction; inserting at least one fixation bone pin in a plurality of fixed holes to maintain the universal osteotomy device; cutting along a guide slot to produce an osteotomy; spreading the osteotomy; placing a bone plate to maintain the osteotomy. Wherein the surface of the first body component and the surface of the second body component have an average curvature or a uniform curvature of the bone surface. Wherein the universal osteotomy device comprises: a first body component, a second body component and an extracorporeal alignment component. The first body component has an upper guide edge for forming a cutting track; the second body component has a lower guide edge below the upper guide edge, a guide slot is formed between the upper guide edge and the lower guide edge for guiding a saw blade to perform a cutting procedure. The upper guide edge and the lower guide edge extend outwardly from the first body component and the second body component, respectively. The guide slot has a connecting member for connecting the upper guide edge and the lower guide edge. The extracorporeal alignment component has an engaging member and at least one aiming hole. The engaging member is engaged with the connecting member. The aiming hole is used to confirm the direction of cutting. The aiming hole confirms the direction of cutting by passing through at least one aiming bone pin. The surfaces of the first body component and the second body component have a plurality of fixed holes, the universal osteotomy device is fixed on the surface of the bone by inserting at least one fixation bone pin in the plurality of fixed holes.

According to the embodiment of the present invention, wherein the step of inserting the aiming bone pin in the aiming hole comprises: inserting a bone pin in an angle fixation hole to maintain the angle of the universal osteotomy device. Wherein the extracorporeal alignment component has an engaging member, at least one aiming hole and an angle fixation hole. The engaging member is engaged with the connecting member. The aiming hole is used to confirm the direction of cutting. The angle fixation hole is disposed in the engaging member, the angle/position of the universal osteotomy device is fixed to the bone by using an angle fixation bone pin.

According to the embodiment of the present invention, wherein the step of cutting along the guide slot comprises: cutting along a lateral guide edge. Then, the step of cutting along a lateral guide edge comprises: inserting at least one osteotome. Wherein the first body component has an upper guide edge, a lateral guide edge and a first correcting through-hole. The lateral guide edge is disposed at the end of the upper guide edge for forming a cutting track. The first correcting through-hole is connected to the first body component by a first bar. The second body component has a lower guide edge, an extended barrier plate and a second correcting through-hole. The lower guide edge disposed below the upper guide edge. The extended barrier plate is disposed at the end of the lower guide edge to prevent over-cutting by the saw blade. The second correcting through-hole is connected to the second body component by a second bar. A guide slot is formed between the upper guide edge and the lower guide edge for guiding a saw blade to perform a cutting procedure. The guide slot has a connecting member for connecting the upper guide edge and the lower guide edge.

According to the embodiment of the present invention, wherein the step of spreading the osteotomy comprises: inserting an alignment bar in the longitudinal axis of the first correcting through-hole and the corresponding longitudinal axis of the second correcting through-hole. Wherein the universal osteotomy device has at least one correction angle between at least one longitudinal axis of the first correcting through-hole and at least one second correcting through-hole. When the correction angle of the osteotomy is the same as that of the preoperative planning, the longitudinal axes of the first correcting through-hole and the corresponding second correcting through-hole will coincide and an alignment bar can pass through both through-holes.

According to the embodiment of the present invention, wherein the correction angles are 1°-45°, preferably 3°-30°, the most preferably 6°-20°; the depth of cutting from the upper guide edge and the lower guide edge to a cutting end point is 10 mm-90 mm, preferably 30 mm-90 mm, the most preferably 50 mm-90 mm; the angle between the upper guide edge and the lateral guide edge is 1°-150°, preferably 60°-140°, the most preferably 90°-120°.

According to the embodiment of the present invention, wherein the step of inserting the alignment bar comprises: maintaining the height of the osteotomy by a distractor. After inserting the alignment bar, the height of the osteotomy can be maintained by a distractor. Then, the surgeon placed a bone plate to maintain the osteotomy to complete the operation.

Compared with the conventional technique, the curvature of the surface of the universal osteotomy device is designed according to the average curvature of the surface of the target bone or a uniform curvature and made by three-dimensional printing (3D printing). Since the curvature of the surface of the universal osteotomy device is made with the average curvature of the target bone surface or a uniform curvature, so the universal osteotomy device can fit various bones of most patients, such as: tibia, femur, fibula, humerus, ulna, radius, clavicle, scapula and so on. The surgeon can perform the first cutting under the guide slot specified by the device. The guide slot allows the surgeon to perform the operation accurately. It also provides a reference for calculating the angle and depth of cutting. The lateral guide edge provides the surgical reference for the second cutting. The extracorporeal alignment component can offer a non-invasive assessment of the angle when the surgery is performed, it can predict whether the angle/position of the osteotomy device placement is correct and it can directly fix the osteotomy device onto the bone. The extended barrier plate can avoid over-cutting during bony cutting. In addition, the curvature of the surface of the universal osteotomy device is made with the average curvature of the target bone surface or a uniform curvature. Therefore, it does not require preoperative assessment of the bony curvature, it can be applied to the need for emergency surgery and the manufacturing process is simpler. The present invention further improves the original osteotomy device.

BRIEF DESCRIPTION OF THE DRAWINGS

FIG. 17 illustrates the depth of the present invention from the upper guide edge and the lower guide edge to the cutting end point.

The components, characteristics and advantages of the present invention may be understood by the detailed description of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims. The layout of components may be more complicated in practice.

The present invention provides a surgical method of universal osteotomy device which can be used in various osteotomy, corrective operation or reduction surgery. The surgical method of universal osteotomy device can be used for other bones 603, such as: tibia, femur, fibula, humerus, ulna, radius, clavicle, scapula and so on. In the present embodiment, the surgical method of universal osteotomy device is used to guide a saw blade 703 to perform high tibial osteotomy.

Figure 1:
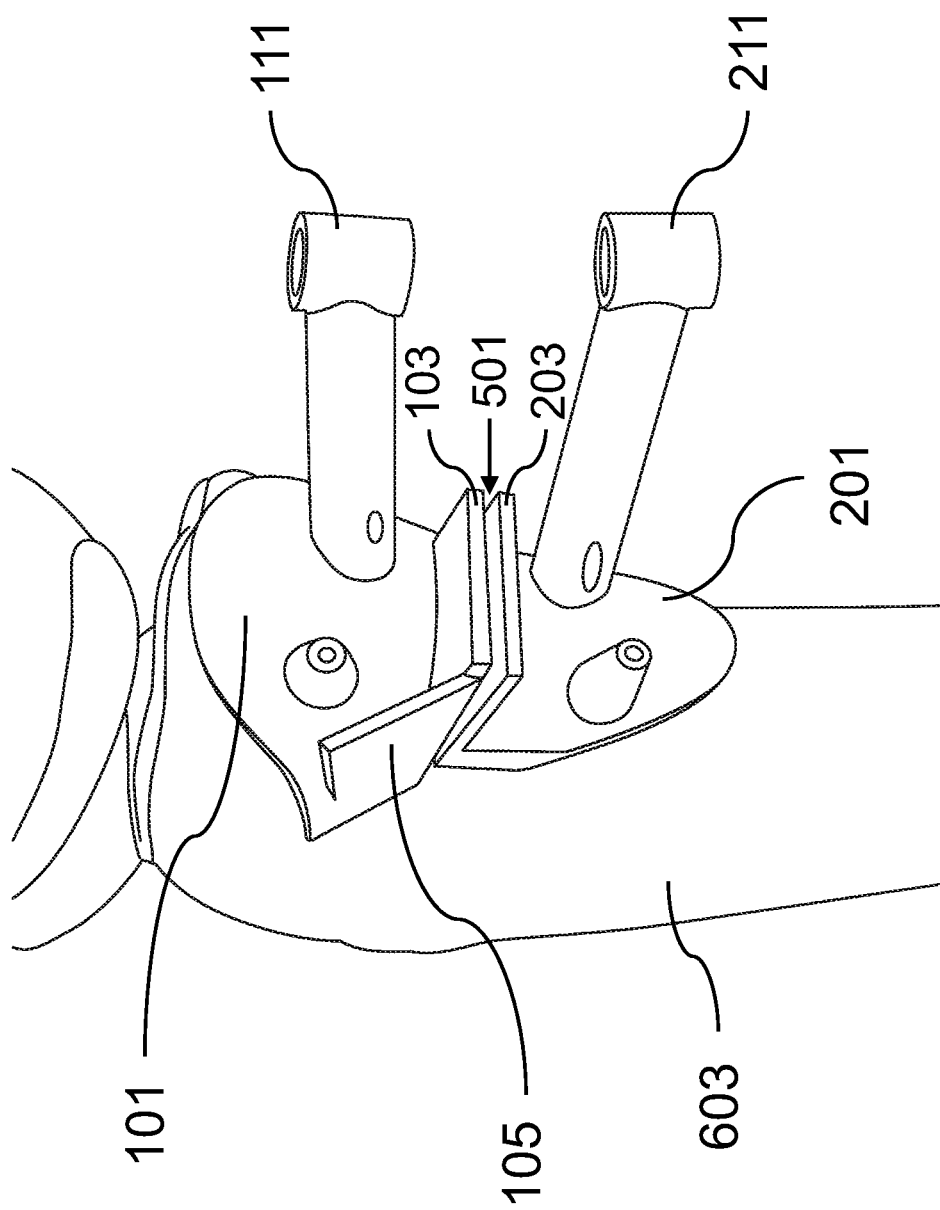
FIG. 1 illustrates the step of placing a first body component and a second body component on the surface of a bone.
Figure 2:
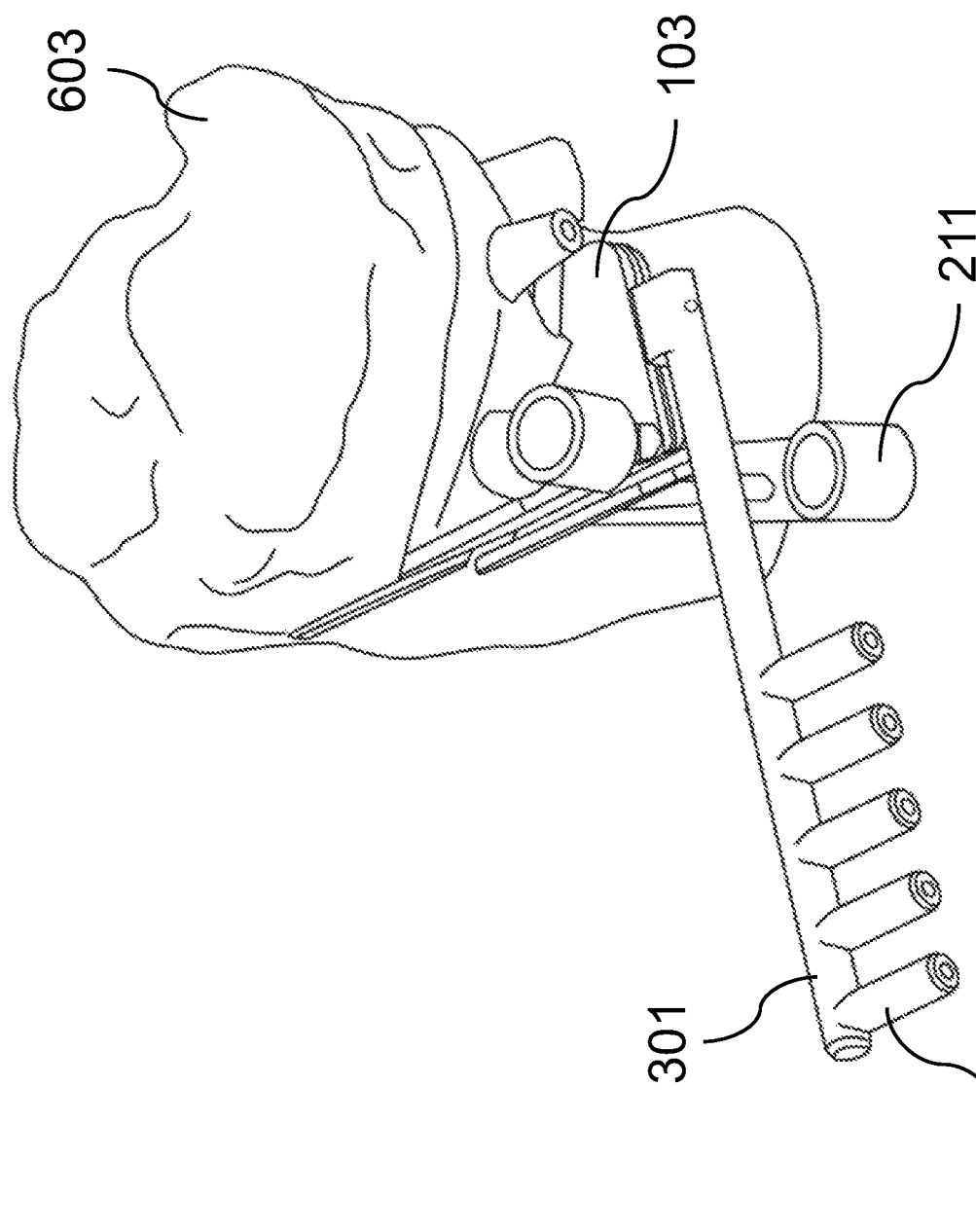
FIG. 2 illustrates the step of engaging an engaging member with a connecting member.
Figure 3:
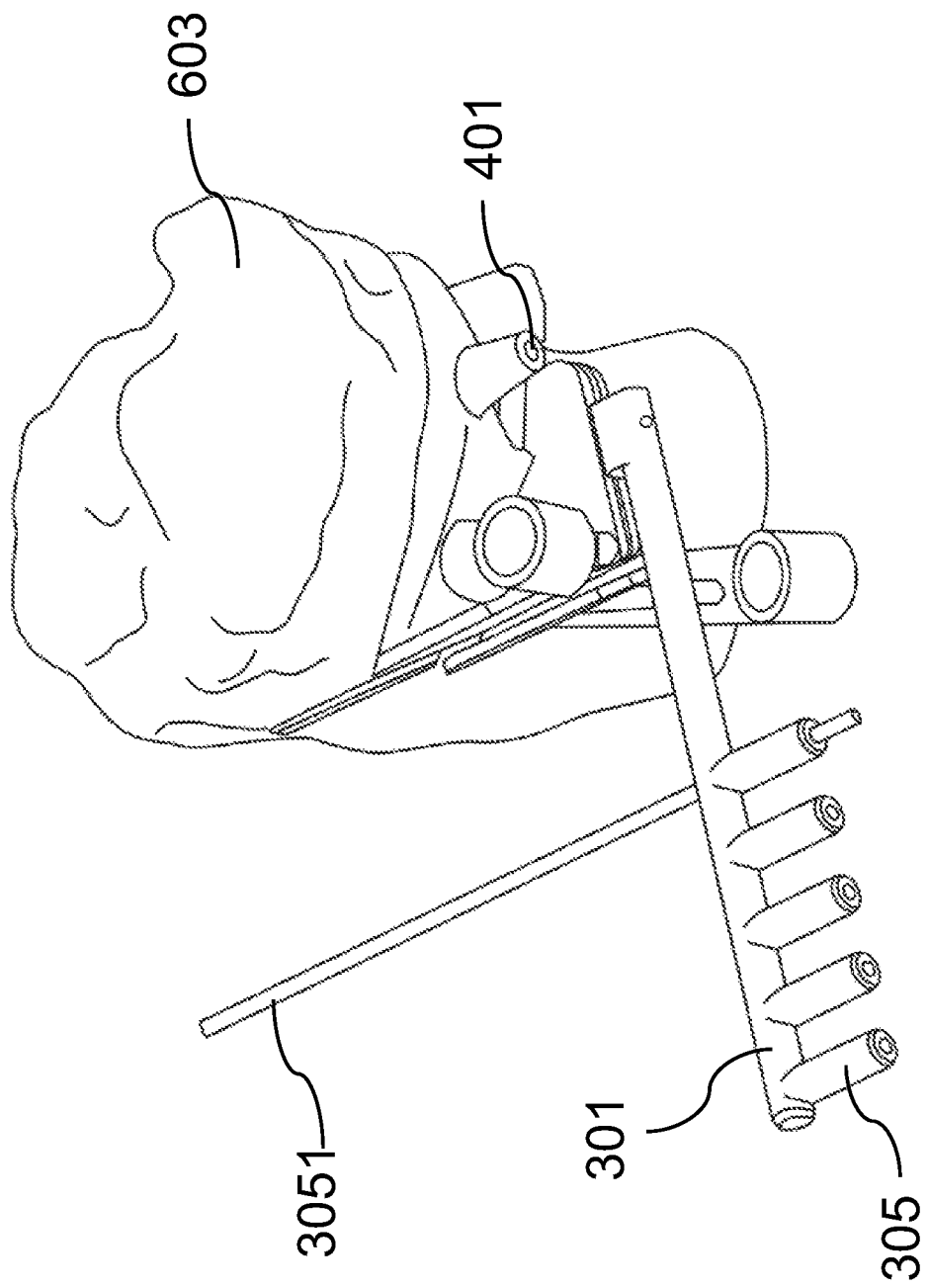
FIG. 3 illustrates the step of inserting at least one aiming bone pin in at least one aiming hole to confirm the cutting direction.
Figure 5:
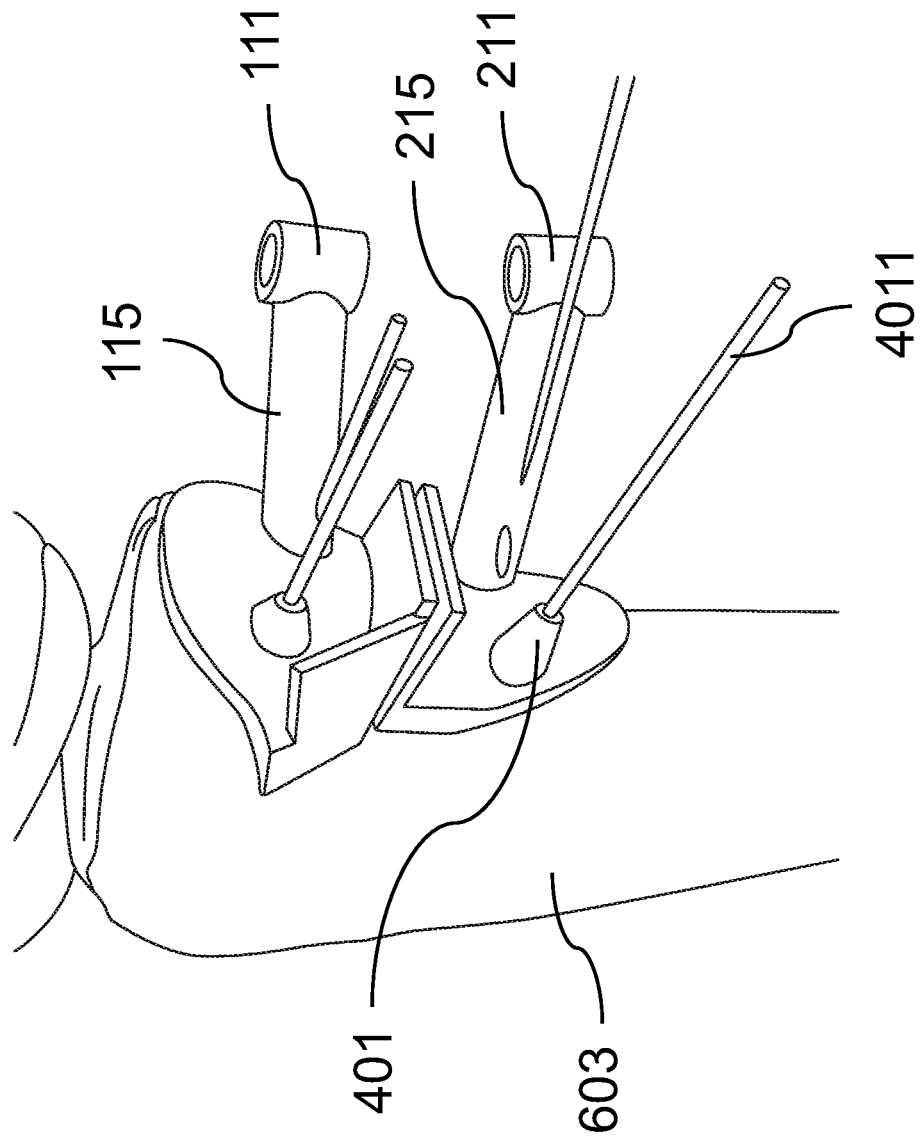
FIG. 5 illustrates the step of inserting at least one fixation bone pin in a plurality of fixed holes to maintain the universal osteotomy device.
Figure 6:
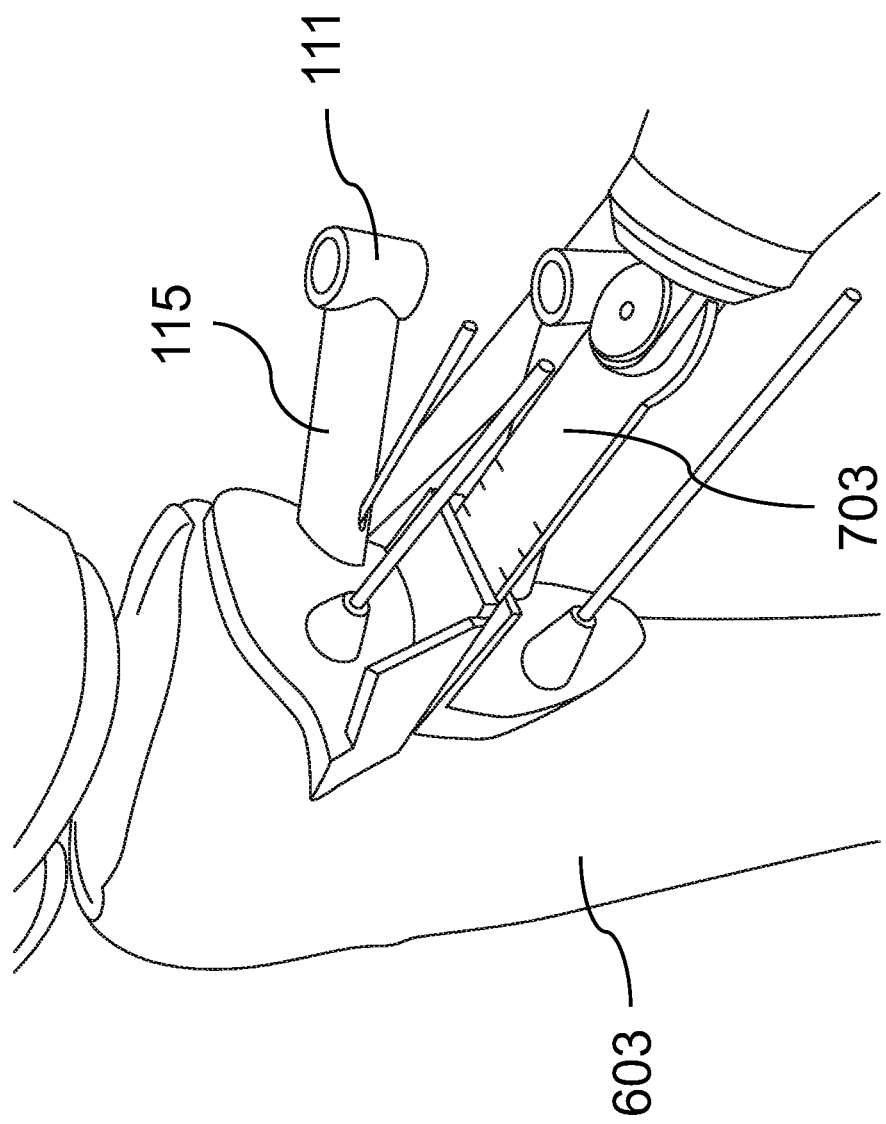
FIG. 6 illustrates the step of cutting along a guide slot to produce an osteotomy.
Figure 9:
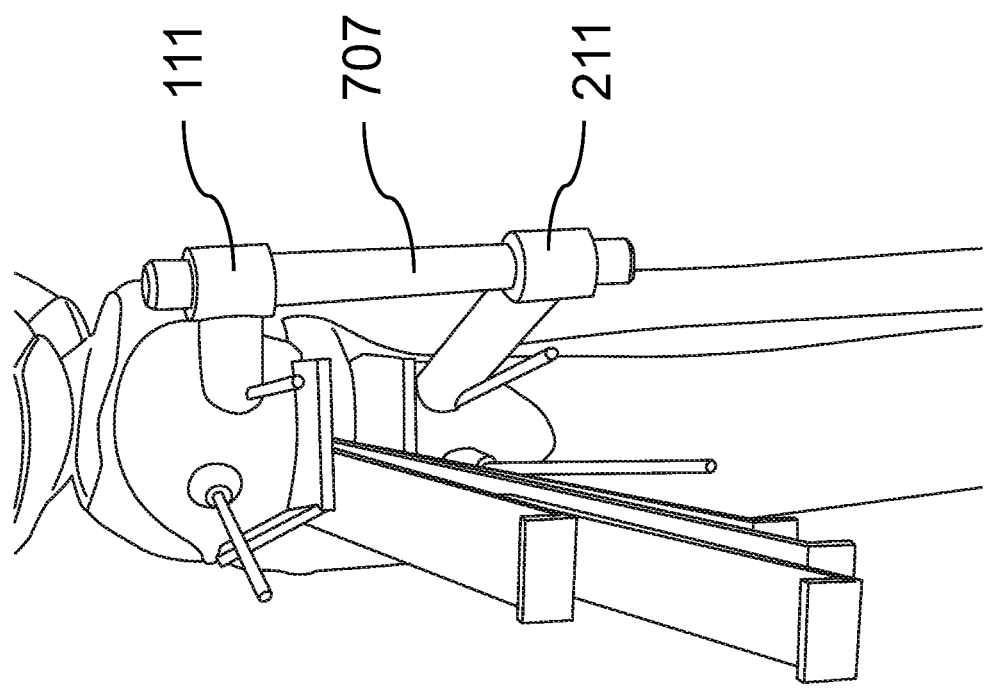
FIG. 9 illustrates the step of spreading the osteotomy and inserting an alignment bar in the longitudinal axis of the first correcting through-hole and the longitudinal axis of the second correcting through-hole.
Figure 11:
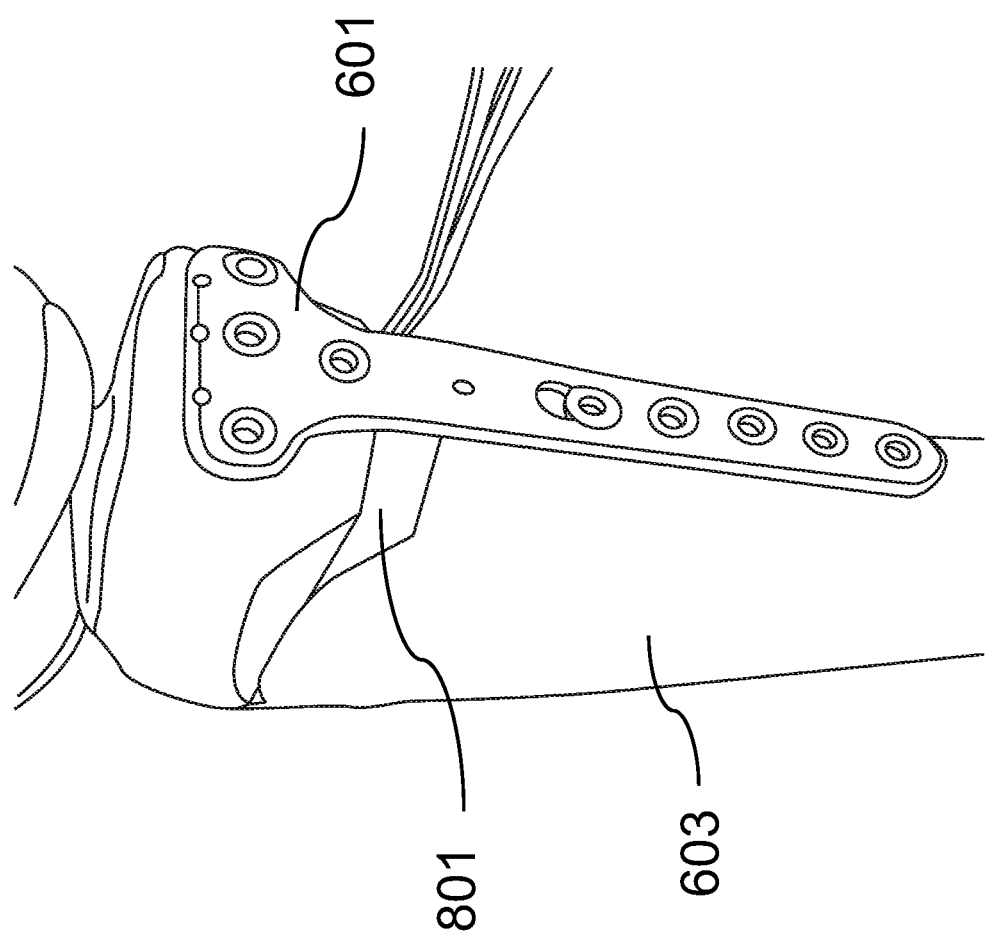
FIG. 11 illustrates the step of placing a bone plate to maintain the osteotomy.
Figure 12:
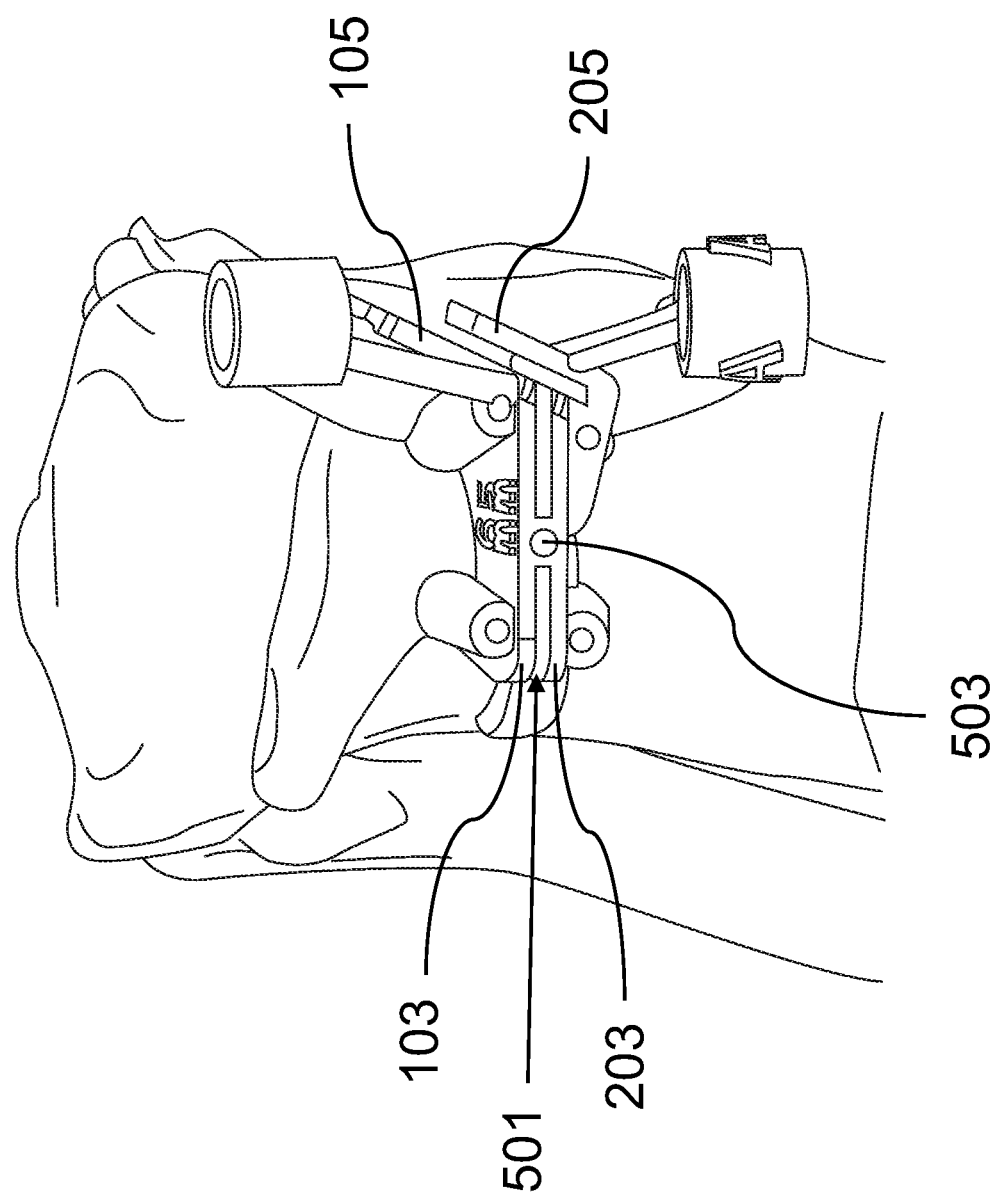
FIG. 12 illustrates a front view of universal osteotomy device without an extracorporeal alignment component.
Figure 13:
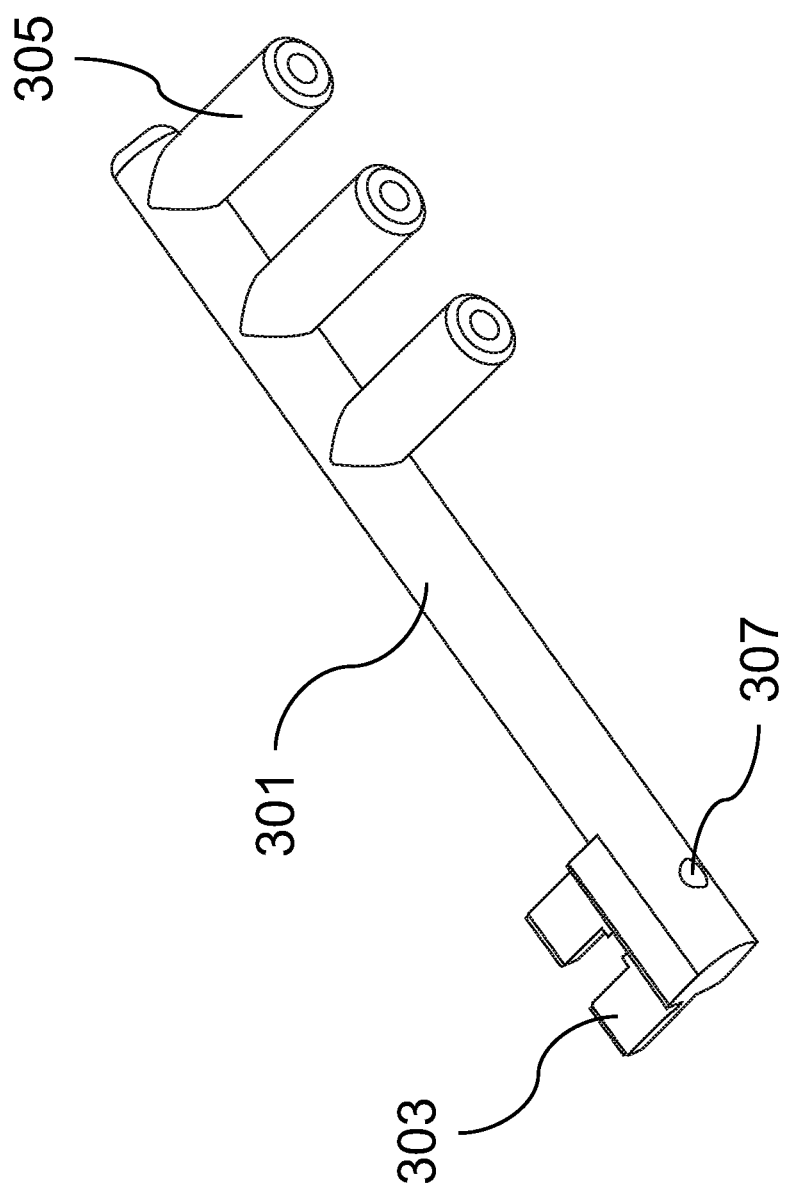
FIG. 13 illustrates an in vitro extracorporeal alignment component.

Please refer to FIG. 1, FIG. 2, FIG. 3, FIG. 5, FIG. 6, FIG. 9, FIG. 11, FIG. 12 and FIG. 13. FIG. 1 illustrates the step of placing a first body component 101 and a second body component 201 on the surface of a bone 603. FIG. 2 illustrates the step of engaging an engaging member 303 with a connecting member 503. FIG. 3 illustrates the step of inserting at least one aiming bone pin 3051 in at least one aiming hole 305 to confirm the cutting direction. FIG. 5 illustrates the step of inserting at least one fixation bone pin 4011 in a plurality of fixed holes 401 to maintain the universal osteotomy device. FIG. 6 illustrates the step of cutting along a guide slot 501 to produce an osteotomy 801. FIG. 9 illustrates the step of spreading the osteotomy 801 and inserting an alignment bar 707 in the longitudinal axis 113 of the first correcting through-hole 111 and the longitudinal axis 213 of the second correcting through-hole 211. FIG. 11 illustrates the step of placing a bone plate 601 to maintain the osteotomy 801. FIG. 12 illustrates a front view of universal osteotomy device without an extracorporeal alignment component 301. FIG. 13 illustrates an extracorporeal alignment component 301.

In one embodiment of the present invention, the surgical method of universal osteotomy device comprises the steps of: placing a first body component 101 and a second body component 201 on the surface of a bone 603; engaging an engaging member 303 with a connecting member 503; inserting at least one aiming bone pin 3051 in at least one aiming hole 305 to confirm the cutting direction; inserting at least one fixation bone pin 4011 in a plurality of fixed holes 401 to maintain the universal osteotomy device; cutting along a guide slot 501 to produce an osteotomy 801; spreading the osteotomy 801; placing a bone plate 601 to maintain the osteotomy 801. Wherein the surface of the first body component 101 and the surface of the second body component 201 have an average curvature of the bone surface or a uniform curvature. When the universal osteotomy device is arranged on the surface of the tibia, the extracorporeal alignment component 301 is mounted on the connecting member 503 of the universal osteotomy device through the engaging member 303. The engaging member 303 and the aiming hole 305 are respectively located at both ends of the extracorporeal alignment component 301. When the universal osteotomy device is placed on the bone surface, the extracorporeal alignment component 301 has a rectangular appearance and the extracorporeal alignment component 301 is placed laterally on the universal osteotomy device so that the aiming hole 305 can be located on the outside of human body. The angle/position of placement of the universal osteotomy device can be evaluated in a noninvasive manner by the aiming hole 305. Therefore, it is possible to predict whether the placement (orientation/position) of the universal osteotomy device is appropriate. Then, the surgeon inserts the saw blade 703 and starts cutting according to the upper guide edge 103 and the lower guide edge 203 of the universal osteotomy device. The surgeon can use the upper guide edge 103 and the lower guide edge 203 as a reference for the evaluation of the depth of cut. In another way, make a mark on the saw blade 703, the surgeon can check the cutting depth by eyes.

Wherein the universal osteotomy device comprises: a first body component 101, a second body component 201 and an extracorporeal alignment component 301. Wherein the first body component 101 has an upper guide edge 103 for guiding a cutting track; the second body component 201 has a lower guide edge 203 disposed below the upper guide edge 103, a guide slot 501 is formed between the upper guide edge 103 and the lower guide edge 203 for guiding a saw blade 703 to perform a cutting procedure. The upper guide edge 103 and the lower guide edge 203 extend outwardly from the first body component 101 and the second body component 201, respectively. The guide slot 501 has a connecting member 503 for connecting the upper guide edge 103 and the lower guide edge 203. The extracorporeal alignment component 301 has an engaging member 303 and at least one aiming hole 305. The engaging member 303 is engaged with the connecting member 503. The aiming hole 305 confirms the direction of cutting by passing through at least one aiming bone pin 3051. Wherein the surface of the first body component 101 and the surface of the second body component 201 have an average curvature of the bone surface or a uniform curvature. When the operation is performed, the surgeon can directly cut the connecting member 503 with the bone saw. In addition, the surfaces of the first body component 101 and the second body component 201 have a plurality of fixed holes 401, the universal osteotomy device is fixed on the surface of the bone 603 by inserting at least one fixation bone pin 4011 in the plurality of fixed holes 401. Whereby the universal osteotomy device is fixed more firmly to the surface of the bone 603. It can avoid the oscillation of saw blade 703 causing the movement of universal osteotomy device during cutting. It makes the cutting position more accurate. Furthermore, the aiming hole 305 is cylindrical in the present embodiment, but not limited to, it may be changed to other shapes as necessary. A number of aiming hole 305 are distributed on the extracorporeal alignment component 301. Its cylindrical design allows the aiming bone pin 3051 to pass through. It is possible to determine whether the universal osteotomy device of the present invention is set at the correct angle/position by the guidance of the aiming bone pin 3051. The aiming bone pin 3051 is the in vitro guideline to determine the angle/position of the device. It is a noninvasive assessment.

In addition, the surface of the first body component 101 and the surface of the second body component 201 have an average curvature of the target bone surface and a uniform specification. So that the universal osteotomy device of the present invention can fit the bone surface of most patients and it is designed for medical emergencies. It can be used immediately in emergency and it does not require a complicated assessment before surgery. Thus, it is possible to achieve the accurate, rapid and convenient purpose for performing osteotomy.

Figure 4:
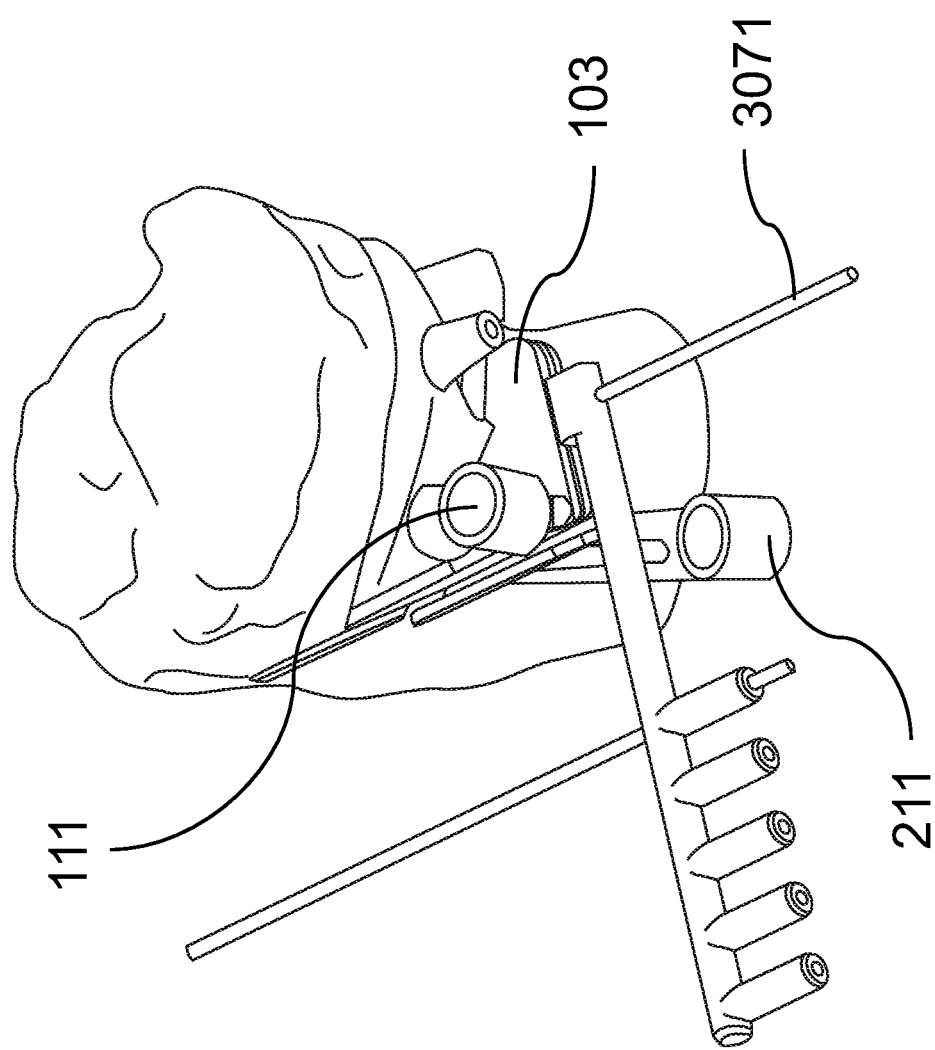
FIG. 4 illustrates the step of inserting an angle fixation bone pin in an angle fixation hole to maintain the angle of the universal osteotomy device.

Please refer to FIG. 4. FIG. 4 illustrates the step of inserting an angle fixation bone pin 3071 in an angle fixation hole 307 to maintain the angle/position of the universal osteotomy device.

In another embodiment of the present invention, wherein the step of inserting the aiming bone pin 3051 in the aiming hole 305 comprises: inserting an angle fixation bone pin 3071 in an angle fixation hole 307 to maintain the angle of the universal osteotomy device. Once the aiming hole 305 confirms that the angle/position of the universal osteotomy device is correct, the universal osteotomy device can be fixed on the bone 603 directly by inserting the angle fixation bone pin 3071 from the angle fixation hole 307 of the extracorporeal alignment component 301. Compared with the osteotomy device in the prior art, the present invention provides a more precise cutting angle and position. The precise cutting is a very important point in osteotomy. Because the spreading angle of the bone 603 is based on it. Therefore, it affects the correction of the biomechanical axis of the low limb.

Wherein the extracorporeal alignment component 301 has an engaging member 303, at least one aiming hole 305 and an angle fixation hole 307. The engaging member 303 is engaged with the connecting member 503. The aiming hole 305 is used to confirm the direction of cutting. The angle fixation hole 307 is disposed in the engaging member 303, the angle/position of the universal osteotomy device is fixed to the bone 603 by using an angle fixation bone pin 3071. In order to reinforce the fixation strength of the universal osteotomy device on the bone surface, at least one fixation bone pin 4011 can be inserted in the fixed holes 401 after the universal osteotomy device is fixed on the bone 603 directly by inserting the angle fixation bone pin 3071 from the angle fixation hole 307 of the extracorporeal alignment component 301.

Figure 7:
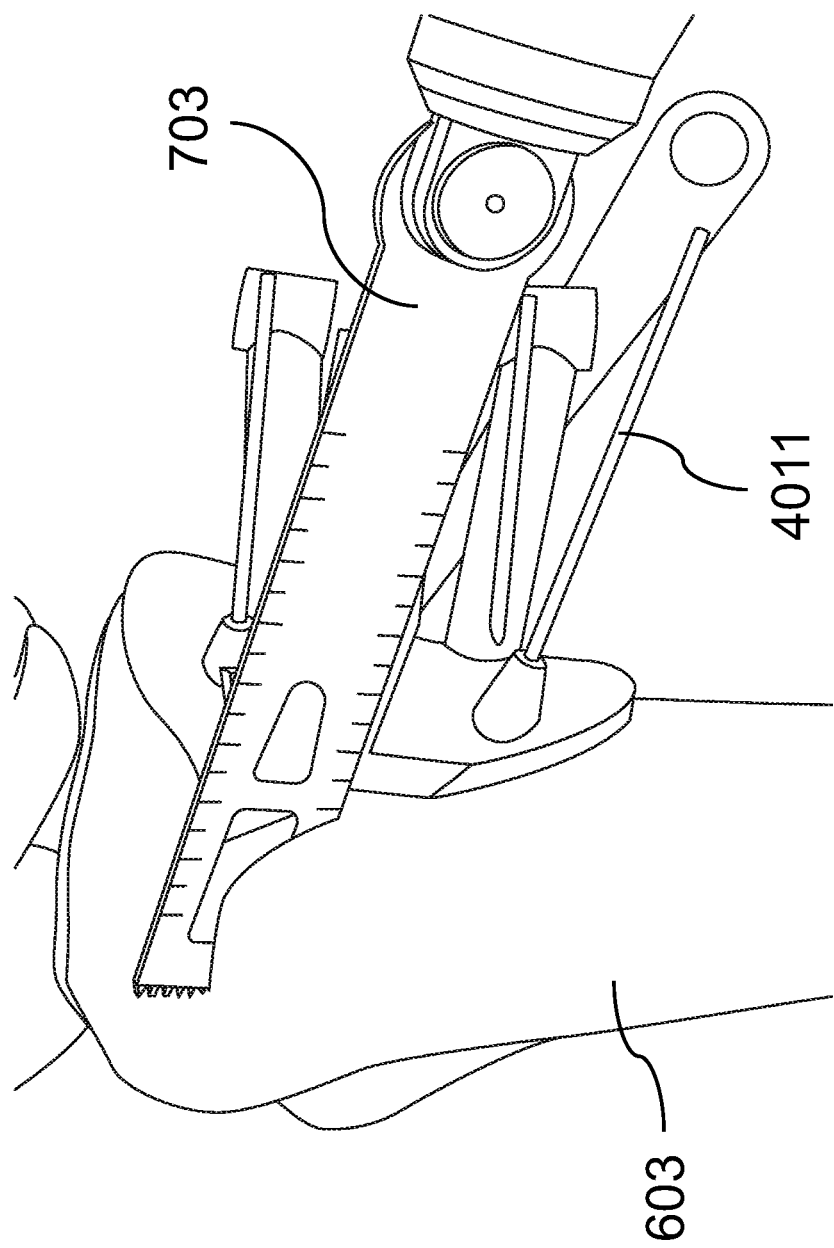
FIG. 7 illustrates the step of cutting along a lateral guide edge.
Figure 8:
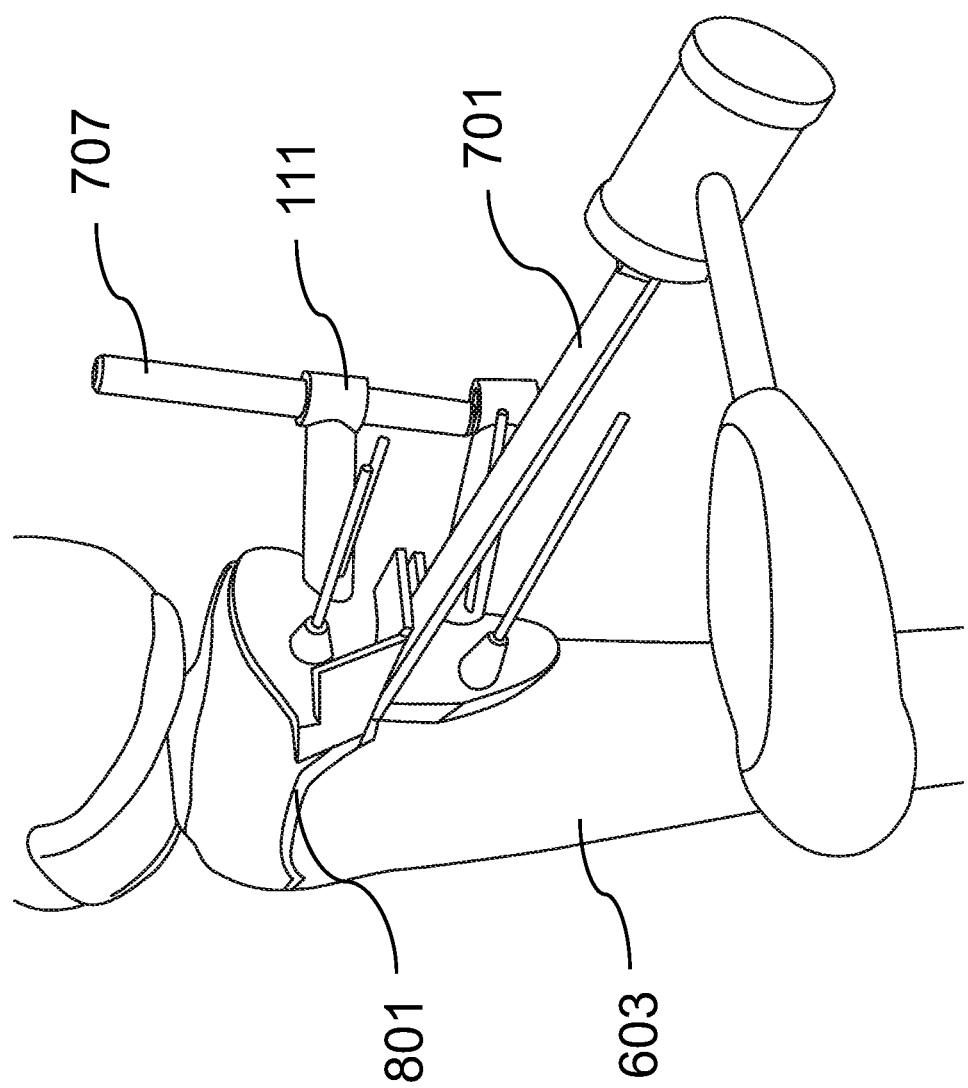
FIG. 8 illustrates the step of inserting at least one osteotome.

Please refer to FIG. 7 and FIG. 8. FIG. 7 illustrates the step of cutting along a lateral guide edge 105. FIG. 8 illustrates the step of inserting at least one osteotome 701.

In one embodiment of the present invention, wherein the step of cutting along the guide slot 501 comprises: cutting along a lateral guide edge 105. Then, the step of cutting along a lateral guide edge 105 comprises: inserting at least one osteotome 701. The surgeon can use the upper guide edge 103 and the lower guide edge 203 as a reference for the evaluation of the depth of cut. The saw blade 703 cuts to a predetermined depth and cuts along the upper guide edge 103 and the lower guide edge 203. Then, it cuts along the second cutting position guided by the lateral guide edge 105 to produce an oblique osteotomy 801. Moreover, the surgeon inserts the osteotome 701 to spread the osteotomy 801.

Wherein the first body component 101 has an upper guide edge 103 and a lateral guide edge 105. The lateral guide edge 105 is disposed at the end of the upper guide edge 103 for guiding a cutting track. The lateral guide edge 105 is used to guide the saw blade 703 to perform a cutting procedure of the second cutting position. The second body component 201 has a lower guide edge 203 and an extended barrier plate 205. The lower guide edge 203 disposed below the upper guide edge 103. The extended barrier plate 205 is disposed at the end of the lower guide edge 203 to prevent over-cutting. The upper guide edge 103 and the lower guide edge 203 extend outwardly from the first body component 101 and the second body component 201, respectively. A guide slot 501 is formed between the upper guide edge 103 and the lower guide edge 203 for guiding the saw blade 703 to perform a cutting procedure of the first cutting position. The guide slot 501 has a connecting member 503 for connecting the upper guide edge 103 and the lower guide edge 203. The upper guide edge 103, the lower guide edge 203 and the lateral guide edge 105 are used to perform high tibial osteotomy. In the previous technology of osteotomy device, it is found that over-cutting often occurs during bone cutting along lateral guide edge 105. The extra cutting will make the bones 603 become weaker. Bones 603 may break during fixation of the bone plate 601 leading to a prolonged recovery period. In order to avoid the over-cutting, the present invention further improves the design. An extended barrier plate 205 is added to the second body component 201 relative to the lateral guide edge 105. When the saw blade 703 cuts to a predetermined position, it can be blocked by the extended barrier plate 205 to avoid over-cutting. In the practice of osteotomy, the present invention ensures a more precise surgery, prevents over-cutting and shortens the recovery period by preoperative planning.

Figure 10:
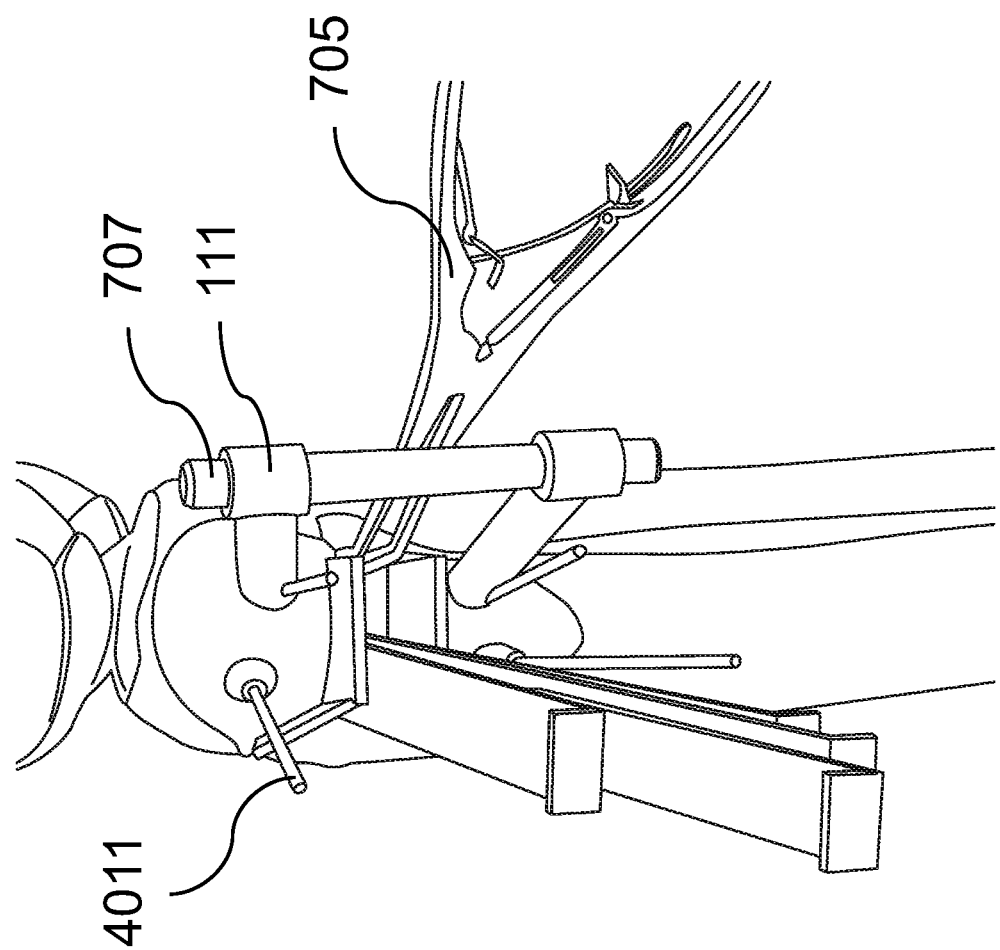
FIG. 10 illustrates the step of maintaining the height of the osteotomy by a distractor.
Figure 14:
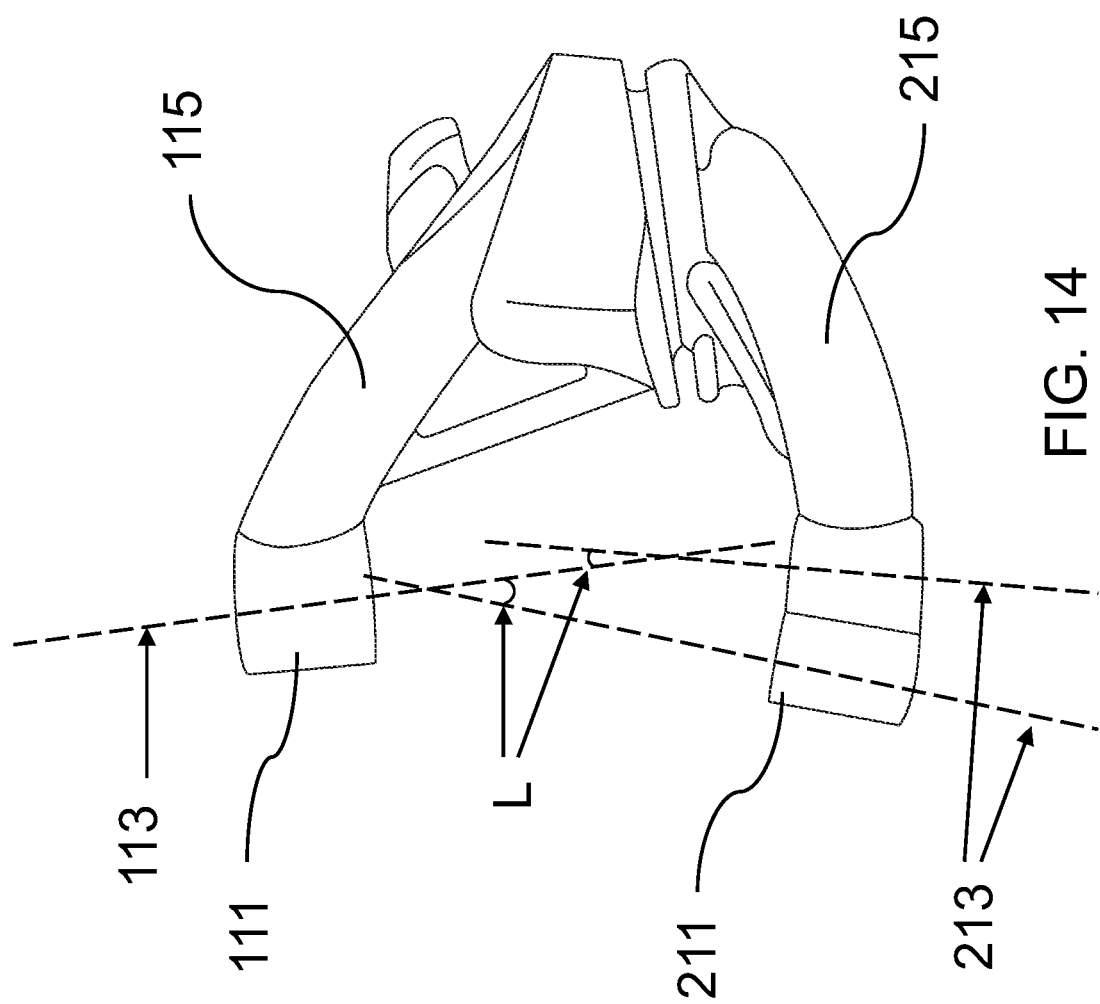
FIG. 14 illustrates a side view of universal osteotomy device.
Figure 15:
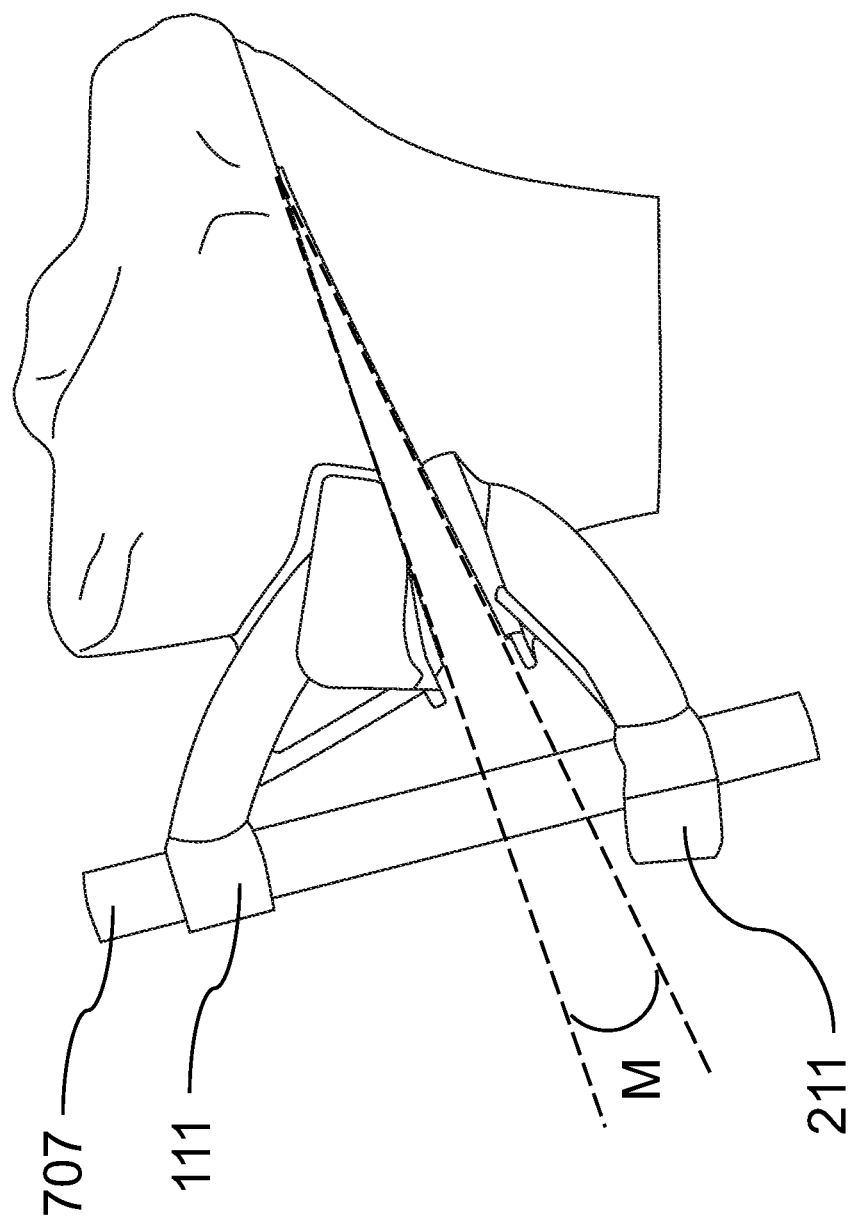
FIG. 15 illustrates that the osteotomy is spread to the correction angle by the first body component and the second body component.
Figure 16:
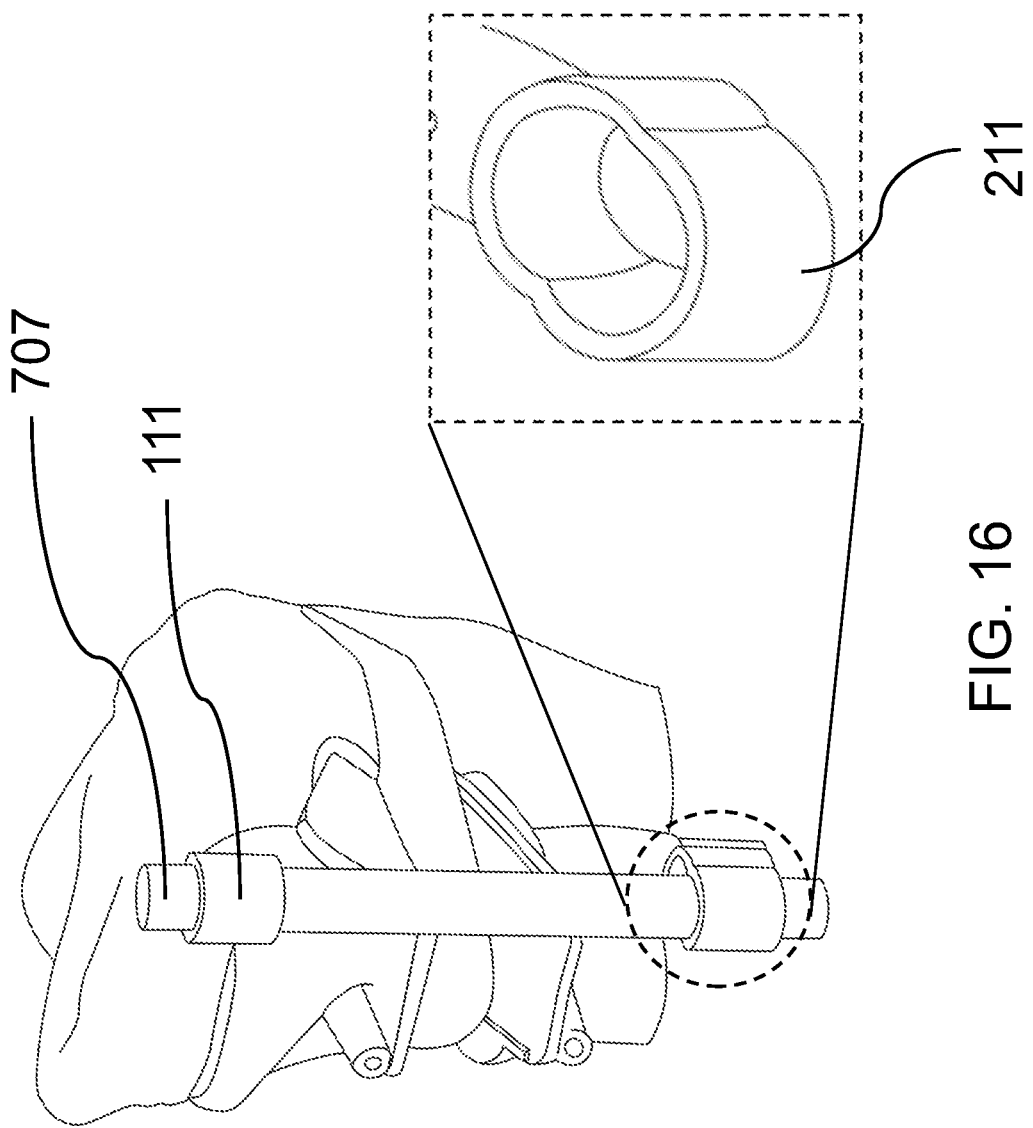
FIG. 16 illustrates that the osteotomy is spread to another correction angle by the first body component and the second body component.

Please refer to FIG. 9, FIG. 10, FIG. 14, FIG. 15, FIG. 16 and FIG. 17. FIG. 9 illustrates the step of spreading the osteotomy 801 and inserting an alignment bar 707 in the longitudinal axis 113 of the first correcting through-hole 111 and the corresponding longitudinal axis 213 of the second correcting through-hole 211. FIG. 10 illustrates the step of maintaining the height of the osteotomy 801 by a distractor 705. FIG. 14 illustrates a side view of universal osteotomy device. FIG. 15 illustrates that the bone 603 is spread to the correction angle M by the first body component 101 and the second body component 201. FIG. 16 illustrates that the bone 603 is spread to another correction angle by the first body component 101 and the second body component 201. FIG. 17 illustrates the depth of the present invention from the upper guide edge 103 and the lower guide edge 203 to the cutting end point 803.

In another embodiment of the present invention, wherein the step of spreading the osteotomy 801 comprises: inserting an alignment bar 707 in the longitudinal axis 113 of the first correcting through-hole 111 and the corresponding longitudinal axis 213 of the second correcting through-hole 211. Then, the step of inserting the alignment bar 707 comprises: maintaining the height of the osteotomy 801 by a distractor 705. The saw blade 703 cuts to a predetermined depth and cuts along the upper guide edge 103 and the lower guide edge 203. Then, it cuts along the second cutting position guided by the lateral guide edge 105 to produce an oblique osteotomy 801. After the osteotomy 801 is done, the first cutting position of the tibia is spread to the predetermined correction angle M where the universal osteotomy device is fixed to the tibia. The alignment bar 707 is then inserted through the first correcting through-hole 111 and the second correcting through-hole 211. After confirming the correction angle M of the osteotomy 801, the height of the osteotomy 801 can be temporarily maintained by a distractor 705. Then, the surgeon placed a bone plate 601 to maintain the osteotomy 801. The present invention can avoid ligament injury during surgery. It can also cut out an osteotomy 801 to resist the rotation of the bones 603 during patient activity. The present invention is designed according to a preoperative correction plan to ease the surgical procedure.

Wherein the first body component 101 further comprises a first correcting through-hole 111. The first correcting through-hole 111 is connected to the first body component 101 by a first bar 115. The second body component 201 further comprises a second correcting through-hole 211. The second correcting through-hole 211 is connected to the second body component 201 by a second bar 215. In the present invention, the first correcting through-hole 111 and the second correcting through-hole 211 are designed to confirm the correction angle of osteotomy 801. For this reason, there is at least one correction angle L between at least one longitudinal axis 113 of the first correcting through-hole 111 and at least one longitudinal axis 213 of the second correcting through-hole 211. In high tibial osteotomy, the osteotomy 801 has a preoperative planning correction angle M. When the tibia is spread by the first body component 101 and the second body component 201 with the correction angle M, the longitudinal axis 113 of the first correcting through-hole 111 and the corresponding longitudinal axis 213 of the second correcting through-hole 211 can coincide. An alignment bar 707 is passed through the first correcting through-hole 111 and the second correcting through-hole 211 to ensure the correction angle M. Firstly, the aforementioned correction angle M is based on the evaluation of the surgeon. Secondly, the angle between the longitudinal axis 113 of the first correcting through-hole 111 and the corresponding longitudinal axis 213 of the second correcting through-hole 211 is then determined according to the predetermined correction angle M. The alignment bar 707 can be inserted between the first correcting through-hole 111 and the second correcting through-hole 211 only when the tibia is spread at a preoperative planned correction angle M by the first body component 101 and the second body component 201.

The first correcting through-hole 111 or the second correcting through-hole 211 is formed by overlapping of two circles. Since each circle has a central axis, it is possible to form at least one longitudinal axis 113 or at least one longitudinal axis 213. At least one correction angle L between at least one longitudinal axis 113 of the first correcting through-hole 111 and at least one longitudinal axis 213 of the second correcting through-hole 211 are formed. The universal osteotomy device of the present invention can have different correction angles L at the same time since the correction angles L between the longitudinal axes of the correcting through-holes can be formed at different angles. It can extend the scope of application and reduce manufacturing cost.

In one embodiment of the present invention, wherein the correction angles L are 1°-45°, preferably 3°-30°, the most preferably 6°-20°; the depth of cutting from the upper guide edge 103 and the lower guide edge 203 to a cutting end point 803 is 10 mm-90 mm, preferably 30 mm-90 mm, the most preferably 50 mm-90 mm; the angle between the upper guide edge 103 and the lateral guide edge 105 is 1°-150°, preferably 60°-140°, the most preferably 90°-120°. The universal osteotomy device of the present invention can parameterize the correction angles L, the depth of cutting, the angle at which the upper guide edge 103 and the lateral guide edge 105 are formed. It is made in a large number of uniform specifications. Because it has many different parameters to choose from, it can cope with various emergencies. Furthermore, it can be used in line with the needs of patients immediately.

Compared with the conventional technique, the universal osteotomy device is manufactured by three-dimensional printing according to the average curvature of Asian skeletal surface collected before surgery or a uniform curvature. It constructs an integrally formed or combined device. The universal osteotomy device can fit the bones 603 of most patients. The surgeon can perform the first cutting position under the guide slot 501 specified by the device. The guide slot 501 allows the surgeon to perform the operation accurately. It also provides a reference for calculating the angle and depth of cutting. The lateral guide edge 105 provides the surgical reference of the surgeon at the second cutting position. The extracorporeal alignment component 301 and the extended barrier plate 205 further improve the osteotomy device in the prior art. Therefore, the present invention can take a non-invasive assessment of the angle/position when the surgery is performed, it can predict whether the angle/position of the osteotomy device placement is correct, it can directly maintain the angle/position of the osteotomy device placement and it can avoid over-cutting. In addition to improving the surgery itself, the present invention also standardizes the implementation of the surgeon's operation.

The universal osteotomy device simplifies the prior art osteotomy device. It can significantly shorten the time of preoperative assessment. The curvature of the surface of the universal osteotomy device is made with the average curvature of the target bone surface or a uniform curvature. In addition to shortening the preoperative evaluation time, there is no need to spend extra design time. In the manufacturing process, the universal osteotomy device has a unified specification and shortens the overall manufacturing process. Therefore, the universal osteotomy device can be manufactured in large quantities and it can be used quickly. For emergency medical conditions, the universal osteotomy device provides an accurate, rapid and universal way.

Various terms used in this disclosure should be construed broadly. For example, if an element "A" is to be coupled to or with element "B," element A may be directly coupled to element B or be indirectly coupled through, for example, element C. When the specification states that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification refers to "a" or "an" element, this does not mean there is only one of the described elements.

The foregoing descriptions are preferred embodiments of the present invention. As is understood by a person skilled in the art, the aforementioned preferred embodiments of the present invention are illustrative of the present invention rather than limiting the present invention. The present invention is intended to cover various modifications and similar arrangements included within the spirit and scope of the appended claims, the scope of which should be accorded the broadest interpretation so as to encompass all such modifications and similar structures.

Many of the methods are described in their most basic form, but processes can be added to or deleted from any of the methods and information can be added or subtracted from any of the described messages without departing from the basic scope of the present invention. It will be apparent to those skilled in the art that many further modifications and adaptations can be made. The particular embodiments are not provided to limit the invention but to illustrate it. The scope of the embodiments of the present invention is not to be determined by the specific examples provided above but only by the claims below.

We claim:

1. A surgical method of universal osteotomy device comprising the steps of:
   placing a first body component and a second body component on a surface of a bone;
   engaging an engaging member with a connecting member;
   inserting at least one aiming bone pin in at least one aiming hole to confirm a cutting direction;
   cutting along a guide slot to produce an osteotomy;
   spreading said osteotomy;
   placing a bone plate to maintain said osteotomy;
   wherein a surface of said first body component and a surface of said second body component have an average curvature of bone surface or a uniform curvature.

2. The surgical method of universal osteotomy device of claim 1, wherein said first body component has an upper guide edge; said second body component has a lower guide edge disposed below said upper guide edge.

3. The surgical method of universal osteotomy device of claim 2, wherein said guide slot is formed between said upper guide edge and said lower guide edge; said connecting member is disposed in said guide slot.

4. The surgical method of universal osteotomy device of claim 3, wherein said engaging member and said aiming hole are disposed on an extracorporeal alignment component.

5. The surgical method of universal osteotomy device of claim 4, wherein the step of inserting said aiming bone pin in said aiming hole comprises:
   inserting an angle fixation bone pin in an angle fixation hole to maintain an angle of said universal osteotomy device.

6. The surgical method of universal osteotomy device of claim 5, wherein said angle fixation hole is disposed in said engaging member.

7. The surgical method of universal osteotomy device of claim 6, wherein the step of inserting said angle fixation bone pin in said angle fixation hole comprises:
   inserting a plurality of fixation bone pins in a plurality of fixed holes to maintain said universal osteotomy device.

8. The surgical method of universal osteotomy device of claim 7, wherein said fixed holes are disposed on said first body component and said second body component.

9. The surgical method of universal osteotomy device of claim 8, wherein the step of cutting along said guide slot comprises:
   cutting along a lateral guide edge.

10. The surgical method of universal osteotomy device of claim 9, wherein said lateral guide edge is disposed at an end of said upper guide edge.

11. The surgical method of universal osteotomy device of claim 10, wherein an extended barrier plate is disposed at an end of said lower guide edge to prevent over-cutting on said lateral guide edge.

12. The surgical method of universal osteotomy device of claim 11, wherein the step of cutting along said lateral guide edge comprises:
   inserting at least one osteotome.

13. The surgical method of universal osteotomy device of claim 12, said first body component further comprising:
   a first correcting through-hole being connected to said first body component by a first bar.

14. The surgical method of universal osteotomy device of claim 13, said second body component further comprising:
   a second correcting through-hole being connected to said second body component by a second bar.

15. The surgical method of universal osteotomy device of claim 14, wherein at least one correction angle between at least one longitudinal axis of said first correcting through-hole and at least one longitudinal axis of said second correcting through-hole are formed.

16. The surgical method of universal osteotomy device of claim 15, wherein the step of spreading said osteotomy comprises:
   inserting an alignment bar in said longitudinal axis of said first correcting through-hole and the corresponding said longitudinal axis of said second correcting through-hole.

17. The surgical method of universal osteotomy device of claim 16, wherein said at least one correction angle is 1°-45°.

18. The surgical method of universal osteotomy device of claim 17, wherein a depth of cutting from said upper guide edge and said lower guide edge to a cutting end point is 10 mm-90 mm.

19. The surgical method of universal osteotomy device of claim 18, wherein an angle between said upper guide edge and said lateral guide edge is 1°-150°.

20. The surgical method of universal osteotomy device of claim 19, wherein the step of inserting said alignment bar comprises:
   maintaining a height of said osteotomy by a distractor.

* * * * *